United States Patent [19]
Linforth et al.

[11] Patent Number: 5,869,344
[45] Date of Patent: Feb. 9, 1999

[54] APPARATUS AND METHODS FOR THE ANALYSIS OF TRACE CONSTITUENTS IN GASES

[75] Inventors: Robert Steven Timothy Linforth; Andrew John Taylor, both of Kegworth, United Kingdom

[73] Assignee: Micromass UK Limited, Manchester, England

[21] Appl. No.: 896,487

[22] Filed: Jul. 18, 1997

[30] Foreign Application Priority Data

| Jul. 19, 1996 | [GB] | United Kingdom | 9615303 |
| Jul. 19, 1996 | [GB] | United Kingdom | 9615304 |

[51] Int. Cl.$^6$ ............ G01N 27/00; B01D 59/44; H01J 49/00
[52] U.S. Cl. .......... 436/173; 436/38; 436/39; 436/106; 436/116; 436/119; 436/120; 436/124; 436/127; 436/179; 436/181; 250/281; 250/282; 250/286; 250/288; 73/863.71; 73/864.21; 73/864.33; 73/864.81
[58] Field of Search ............ 73/863.71, 864.21, 73/864.33, 864.81; 250/281, 282, 286, 288; 436/38, 39, 106, 116, 119, 120, 124, 127, 179, 181, 173

[56] References Cited

U.S. PATENT DOCUMENTS

| 3,759,249 | 9/1973 | Fletcher et al. . |
| 4,735,777 | 4/1988 | Mitsui et al. . |
| 5,042,501 | 8/1991 | Kenny et al. . |
| 5,043,576 | 8/1991 | Broadhurst et al. . |
| 5,081,871 | 1/1992 | Glaser . |

FOREIGN PATENT DOCUMENTS

| 60-250227 | 12/1985 | Japan . |
| 824998 | 4/1981 | U.S.S.R. . |
| 904660 | 2/1982 | U.S.S.R. . |
| 2 017 935 | 10/1979 | United Kingdom . |
| 2 022 451 | 12/1979 | United Kingdom . |
| 1 582 869 | 1/1981 | United Kingdom . |
| 2 181 597 | 4/1987 | United Kingdom . |

OTHER PUBLICATIONS

Teranishi, et al.; Standardized Human Olfactory Thresholds, Ed. Devos, Publ. (IRL Press, Oxford 1990), pp. 1–3, 90–93, & 102–103.

Schoellor, Klein: Biomedd. Mass Spectrom., 1979 vol. 6 (8) pp. 350–355.

Soeting, Heidema: Chem. Senses 1988 vol. 13 (4) pp. 607–617.

Haring et al.; Flavour Science and Technology, pub. Wiley, Chichester, 1990.

French, Thomson et al.; Mass Spectrometry in Environmental Sciences, ed. Karasek, Hutzinger and Safe, pub. Plenium Press, 1985 pp. 101–120.

Benoit, Davidson, Lovett et al: Anal. Chem. 1983 vol. 65 pp. 805–807.

Lovett, Reid, Buckley: Biomed. Mass Spectrom. 1979 vol. 6 (3) pp. 91–97.

Wilson, Ottley: Biomed. Mass Spectrom. 1981 vol. 8 (12) pp. 606–610.

Suehiro, Schoellor, Klein: Bun. Kagaku 1979 vol. 28 pp. 361–367.

Goodwin, Holme, Leck: Proc. 7$^{th}$ Int. Vac. Congr. pp. 177–180.

(List continued on next page.)

Primary Examiner—Arlen Soderquist
Attorney, Agent, or Firm—Alix, Yale & Ristas, LLP

[57] ABSTRACT

The invention comprises a novel sample introduction system which incorporates a venturi pump to convey a sample gas to an analytical instrument at atmospheric pressure. An APCI, ICP or MIP mass spectrometer is preferred as the analytical instrument. Using such an inlet with an APCI mass spectrometer, the real-time analysis of trace materials present in breath is facilitated, enabling, for example, the release of compounds responsible for aroma and taste to be analysed during eating and drinking. The invention can also be used for headspace analysis and for monitoring the release of fragrances from skin or clothing.

29 Claims, 2 Drawing Sheets

OTHER PUBLICATIONS

Furner, Alarcon, Irving: J. Am. Soc. Mass Spectrom. 1992 vol. 3 pp. 742–749.

Benoit, Davison, et al.; Int. Arch. Occup. Environ. Health, 1985 vol. 55 pp. 113–120.

Charles Murray Design News, 19 Jul. 1983 pp. 81–82.

Thrall, Kenny: Inhalation Technology 1996 vol. 8 (3) pp. 251–266.

APPARATUS AND METHODS FOR THE ANALYSIS OF TRACE CONSTITUENTS IN GASES

This invention relates to apparatus and methods for the analysis of trace constituents in gases by means of an analytical instrument such as a mass spectrometer, especially a mass spectrometer having an ionization source which operates at atmospheric pressure. In particular it provides methods and apparatus for the real-time analysis of trace constituents present in breath, especially compounds responsible for the aroma and taste of foodstuffs during eating, and those indicative of a medical condition. The invention further provides methods and apparatus for the real-time analysis of fragrances, for example during their release from skin or clothing.

BACKGROUND OF THE INVENTION

The analysis of trace compounds present in samples of air or other gases has many applications, for example in studies of atmospheric pollution and in the analysis of breath, which has application in both medical science and in the food industry. Certain compounds present in breath may serve as markers for a particular disease, and the study of compounds responsible for the flavour and aroma of food released during eating is of interest to the food industry. Particularly in the case of organic trace constituents, the compounds to be analysed are usually present in very small quantities in a large volume of gas. For example, the human nose is very sensitive, and odour thresholds in the sub-ppb level are not uncommon (see Teranishi, et.al., in "Standardised Human Olfactory Thresholds", Ed. Devos, pub. IRL Press, Oxford, 1990). In order to characterise the compounds responsible for aromas and taste it is therefore necessary to use analytical techniques having very high sensitivity and specificity, and mass spectrometry is therefore a preferred technique. Also of interest for medical reasons is the measurement of carbon isotopic ratios in exhaled carbon dioxide, a procedure for which mass spectrometry is obviously essential.

One prior off-line method of admitting samples of breath into an analytical instrument such as a mass spectrometer involves the collection of discrete samples of breath in bags or vessels, the contents of which are subsequently analysed by mass spectroscopy. (See, for example, JP patent application pub. no. 60-250227 and Schoeller and Klein in Biomed. Mass Spectrom., 1979 vol 6 (8) pp 350–355.) This method is most successful for the determination of carbon isotopic ratios in exhaled carbon dioxide. More suitably for the analysis of traces of organic compounds, breath may be passed into absorbent (eg, Tenax) or cryogenic traps which collect the organic compounds but not air. The organic compounds may then be subsequently desorbed from the trap and analysed by, for example, gas chromatography-mass spectrometry. This method is commonly employed for atmospheric air sampling. Linforth and Taylor in Food Chem., 1993 vol 48(2) pp 115–20 describe use of the method for the study of the aroma release from foods. However, the method lacks adequate sensitivity for the detection of many food aromas and, being an off-line method, is difficult to use to study the kinetics of the release of aromas during eating.

A further problem with prior mass spectrometric methods in which at least a portion of a complete breath sample is admitted to the mass spectrometer is the depression of the sensitivity of the spectrometer, especially for spectrometers having conventional electron impact or chemical ionization sources, by the large quantity of water always present in such samples. In view of this, and also because of the very large excess of air, a better prior method of analyzing trace organic compounds in breath is provided by the use of membrane inlet systems. These methods involve the passage of exhaled air over a thin membrane (usually silicone rubber) the other side of which is in communication with the mass spectrometer. In this way air and water is excluded from the spectrometer, but the organic compounds will diffuse through the membrane and enter the mass spectrometer. Soeting and Heidema, in Chem. Senses, 1988 vol 13 (4) pp 607–17, and Haring, et.al, in "Flavour Science and Technology", pub. Wiley, Chichester, 1990 teach the use of such membrane inlet systems for the study of the release of flavour compounds at the nose during eating. Membrane inlet systems have also been used for the analysis of trace organic compounds in atmospheric air.

However, membrane inlet systems also have disadvantages. The membrane may exhibit selectivity, excluding some compounds which have a low affinity for the membrane, and some compounds may exhibit very slow diffusion through the membrane and consequently have extended response times. Membranes are also very thin and consequently fragile and of limited lifetime.

Another mass-spectrometric technique which has been used for the analysis of trace organic compounds in breath is direct-introduction atmospheric pressure ionization mass spectrometry (API). In this technique, ions are formed in a sample gas at high pressure (typically atmospheric pressure) by means of a corona discharge or radiation from a suitable source (eg, $^{63}$Ni) and enter a mass analyzer (which operates at high vacuum) through a very small orifice. In use, a gas to be analyzed is caused to flow through a tube in which a discharge electrode is suspended, and ions formed in the discharge pass through an aperture disposed downstream of the electrode into the mass analyzer. (See, for example, GB patent 1582869). Because the ionization takes place at high pressure, the ions formed in API mass spectrometry are typically cluster ions, often comprising a molecule of a trace organic compound clustered with water molecules. The ionization process is a chemical ionization process which may be represented by the following:

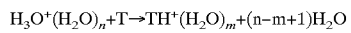

$$H_3O^+(H_2O)_n + T \rightarrow TH^+(H_2O)_m + (n-m+1)H_2O$$

where T represents a trace organic molecule present in the sample. The species $H_3O^+(H_2O)_n$ is a protonated water cluster ion formed in the discharge in air in the presence of water. More details of API mass spectrometry are given by French, Thomson, Davidson, Reid, and Buckley in "Mass Spectrometry in Environmental Sciences", Eds. Karasek, Hutzinger and Safe, pub. Plenum Press, 1985, at pp 101–120. These authors quote detection limits in the low ppb–ppt range for various organic compounds present in atmospheric air. Benoit, Davidson, Lovett, et.al, in Anal. Chem. 1983 vol 55 pp 805–7 report the use of such an API system for breath analysis. The inlet system used comprised a capillary tube through which breath is introduced into a flow of an inert carrier gas which then enters the mass spectrometer. In order to control the dilution ratio, the subject is required to maintain a constant pressure differential across the capillary while exhaling. A similar system, using a flowmeter to control the dilution ratio, was earlier reported by Lovett, Reid, Buckley, et.al in Biomed. Mass Spectrom. 1979 vol 6 (3) pp 91–97. These systems are capable of providing an analysis of each exhalation but are inconvenient because the subject has to control his breathing to maintain a constant dilution ratio. Particularly when monitoring trace compounds indicative of a disease, however, the apparatus taught by U.S. Pat. No. 5,042,501 may be used. The inlet system described therein incorporates a mixing chamber which intended to average out individual exhalations and produce a constant signal from the mass spectrometer. This apparatus is clearly unsuitable when a very fast response time is required, for example during the analysis of breath for aroma constituents during eating. Also, in U.S. Pat. No. 5,042,501, the breath itself provides the entire flow of gas to the API spectrometer, making the provision of a mixing chamber essential to maintain the gas flow to the spectrometer while the subject inhales.

An off-line method of API mass spectrometric analysis of breath samples is taught in U.S. Pat. No. 4,735,777, but this is inapplicable to most of the applications to which the present application is directed. Further, none of the prior methods of API analysis of breath are suitable for sampling breath from the nose rather than from the mouth, which is highly desirable in the study of the aroma release from foods.

OBJECT OF THE INVENTION

It is an object of the present invention, therefore, to provide apparatus for and methods of analyzing trace constituents in a gas, typically at atmospheric pressure, having an improved method of transporting the gas from the point of sampling to an analytical instrument which overcomes the limitations of prior methods. It is another object of the invention to provide apparatus for and methods of the analysis of trace constituents in a gas by mass spectrometers having ion sources operating at atmospheric pressure, for example, API, inductively coupled plasma, (ICP) or microwave induced plasma (MIP) ion sources, incorporating the improved method. It is a yet further object to provide such apparatus and methods adapted for the analysis of breath, particularly during eating, to facilitate the study of the release of flavour and aroma compounds.

SUMMARY OF INVENTION

Viewed from one aspect, therefore, the invention provides an apparatus for analyzing trace constituents in a sample of gas, said apparatus comprising:

an analytical instrument for analyzing at least some of said trace constituents and having an entrance port;

gas sampling probe means through which at least some of said gas may flow and having a proximal end disposed for communication with a gas to be analyzed and a distal end disposed in communication with said entrance port; and means for reducing the pressure in the vicinity of said distal end relative to that at said proximal end so that at least some of the gas to be analyzed flows to said entrance port;

the improvement comprising said means for reducing the pressure comprising venturi means disposed adjacent to said distal end, and means for causing a flow of a transport gas to said venturi means.

In a preferred embodiment the analytical instrument comprises a mass spectrometer, most preferably one having an atmospheric pressure ionization source. In this case apparatus according to the invention may further comprise:

a) ionization means, operable at atmospheric pressure, for ionising at least some of said trace constituents and disposed in said entrance port;

b) inlet aperture means through which ions generated by said ionization means may pass, said inlet aperture means connecting said entrance port with an evacuated chamber; and c) ion mass analyzing means disposed in said evacuated chamber for receiving ions passing through said inlet aperture means and for producing signals indicative of their mass-to-charge ratio and their quantity.

The volume of the entrance port in a mass spectrometer according to the invention should preferably be less than the volume of the entrance port in a conventional APCI mass spectrometer intended for the analysis of liquid samples. Preferably the volume of the gas sampling probe means, venturi means and the entrance port should not exceed 200 ml. This ensures that the residence time of a gaseous sample in the entrance port is minimised and allows rapid changes in composition of the sampled gas to be monitored.

The ion mass analyzing means may comprise any type of mass analyzer, for example a quadrupole mass analyzer, a magnetic sector analyzer, a quadrupole ion trap, an ion-cyclotron resonance spectrometer or a time-of-flight analyzer. Conveniently the inlet aperture means comprises a small aperture (20–30 microns diameter) formed in an electrically conductive diaphragm which separates the entrance port from the evacuated chamber, and the pressure in the evacuated chamber is preferably maintained at less than $10^{-4}$ torr. However, it is within the scope of the invention to employ one or more additional chambers, each separately evacuated, between the inlet aperture means and the ion mass analyzing means to provide a conventional staged pressure reduction system. As in many prior atmospheric pressure ionization mass spectrometers, a curtain gas chamber, disposed immediately adjacent to the inlet aperture means and through which a clean inert gas is caused to flow, may also be provided. The gas in such a chamber is provided at a pressure slightly higher than that in the entrance port so that a small flow of gas passes through the inlet aperture from the curtain gas chamber to the entrance port, minimising the quantity of impurities which may pass from the entrance port to the analyzer.

Preferably, the ionization means comprise a corona electrode and a counter electrode, both disposed in said entrance port, and means for sustaining a corona discharge between them. Conveniently, the counter electrode may comprise a plate-like electrode disposed between the distal end of the gas sampling probe means and the inlet aperture means, and the corona electrode may comprise a pin shaped electrode disposed between the distal end of the sampling probe means and the counter electrode with its axis approximately perpendicular to the direction of gas flow from the sampling probe means. One or more small holes are provided in the counter electrode so that ions generated in the corona discharge sustained between the electrodes may be drifted through them towards the inlet aperture means. The means for sustaining a corona discharge may comprise a high voltage power supply which can provide either a positive or a negative voltage to the corona electrode, respectively allowing the generation of either positive ions or negative ions in the discharge.

Alternatively, other ionization means, for example a $^{63}$Ni radioactive source disposed in the entrance port, may also be employed.

Advantageously, means are also provided for introducing into the transport gas one or more additional chemical ionization reagents, or a calibration sample for the mass spectrometer. For example it has been found that for some constituents present in common aroma or flavour samples, higher ionization efficiency can be obtained by introducing hexane into the transport gas to act as an additional chemical ionization reagent gas.

As an alternative to an API mass spectrometer it is within the scope of the invention for the analytical instrument to comprise a plasma ionisation source, for example an inductively coupled plasma (ICP) or a microwave-induced plasma (MIP) source. In this case the transport gas is typically argon or helium and the sample inlet of the ICP or MIP torch is arranged to receive gas from the distal end of the sampling probe means. ICP or MIP spectrometers are useful for the determination of the elemental or isotopic composition of constituents in the gas to be analysed, for example carbon isotopic ratios in expired carbon dioxide. Other analytical instruments may also be employed, for example optical, IR, or UV spectrometers. In these cases the entrance port of the invention may comprise the sampling cell of the spectrometer. Mass spectrometers having conventional high-vacuum ionization sources such as electron impact or chemical ionization sources may also be employed, in which case the ionization means may be disposed inside the evacuated chamber rather than in the entrance port as in the case of an API spectrometer.

In all the above cases the sampling probe means may comprise a capillary tube, preferably but not essentially made of deactivated fused silica. Use of a capillary tube minimises the dead volume of the inlet system and reduces the response time. Preferably also the capillary tube is heated.

In further preferred embodiments the venturi means comprises an outer tubular member disposed coaxially about the sampling probe means, said tubular member extending a short distance beyond the end of the sampling probe means. Transport gas (typically nitrogen) is caused to flow through the outer tubular member, causing a pressure reduction in the vicinity of the distal end of the sampling probe means by the well-known venturi effect. The distance the outer tubular member extends beyond the distal end of the sampling probe means may be adjusted to provide the desired pressure reduction across the sampling probe means and therefore the flow rate through it. A distance of between 0.2 and 2 cm has been found to give good results. A flow of transport gas of about 5–10 l/minute has been found to give a sufficient pumping effect with components having dimensions in the ranges specified. With the above defined parameters, a flow of between 10 and 100 ml/minute, typically 20 ml/minute of air can be generated through the sampling probe means.

Preferably the linear flow velocity of the sample gas in the sample probe means should be between 10 and 100 m.s$^{-1}$, and most preferably between 35 and 60 m.s$^{-1}$, which typically results in a response time of 0.01–0.10 seconds.

Particularly when an API mass spectrometer is provided the invention is especially suitable for the analysis of trace constituents present in a sample of breath. Therefore, in another preferred embodiment the invention further comprises breathing tube means open at one end to the atmosphere and at the other end in communication with the nose or mouth of a subject whose breath is to be analysed so that at least the exhaled breath of the subject passes through the breathing tube means, wherein the proximal end of said sampling probe means is disposed within said breathing tube means. In this way a small proportion of the exhaled breath of the subject is sampled by the pumping action of the venturi means, without interfering with the normal breathing of the subject, and transferred to the analytical instrument. It will be appreciated that the flow generated by the action of the venturi means is independent of the breathing of the subject, and therefore provides a constant dilution ratio, eliminating the need for the controlled breathing by the subject characteristic of certain prior API methods of breath analysis discussed above. With apparatus according to the invention, therefore, the subject is able to eat and drink while still providing useful breath samples, which is impossible in practice with these prior methods.

Consequently the analysis of constituents responsible for the release of aromas and flavour during the consumption of food is made possible by the invention. Because the ionization process in an API mass spectrometer is a chemical ionization process requiring the participation of water molecules, the presence of water vapour in the breath of the subject is not a disadvantage (and may even be essential), in contrast with many prior mass spectrometric techniques. Further, it has been found that saturation of the mass spectrometer by signals due, for example, to ammonia, does not occur in the present invention, probably because of the dilution of the breath sample by the transport gas which is inherent in the apparatus.

Particularly when used for the analysis of aromas, a calibration sample (for example, dimethylpyrazine) may be introduced into the gas sampling means between samples in order to calibrate the mass spectrometer and check on its performance.

Heating of the sampling probe means, preferably to at least 100° C., is also easily achieved in apparatus according to the invention by preheating the flow of transport gas and arranging it to flow over the bulk of the sampling probe means before reaching the distal end. It is also within the scope of the invention to provide other means for heating the sample probe means, for example electrical heaters, additionally or alternatively to that provided by the transport gas. It has been found that the efficiency of ionization of certain species which are difficult to ionize in a corona discharge at temperatures of 100° C. or less can be greatly increased by heating the sample probe means to between 200° and 300° C.

The invention also provides apparatus substantially as described above for sampling gas containing trace constituents from an enclosed volume, for example the headspace in a vessel containing a liquid or a solid, merely by insertion of the proximal end of the sampling probe means into the enclosed volume from which the gas is to be analyzed.

In another embodiment the invention provides means for monitoring the constituents of fragrances applied to skin, hair or clothing, etc. In such an embodiment the proximal end of the sample probe means is merely disposed adjacent to a surface on which is either emitting a fragrance (for example, an item of food) or to which a fragrance has been applied. Trace constituents of the fragrance released from the surface are then drawn into the sampling probe means as described above and may be analyzed substantially in real-time. In this way the release of fragrance constituents from a particular surface during any given period can be studied.

Viewed from another aspect the invention provides a method of analyzing trace constituents comprised in a sample of gas, said method comprising the steps of:
  providing an analytical instrument for analyzing at least some of said trace constituents, said analytical instrument having an entrance port;
  providing a gas sampling probe means through which at least some of said gas may flow and having a proximal end and a distal end;
  disposing said proximal end of said gas sampling probe means in communication with the gas to be analyzed;
  disposing said distal end of said gas sampling probe means in communication with said entrance port;

reducing the pressure in the vicinity of said distal end relative to that at said proximal end so that at least some of the gas to be analyzed flows to said entrance port; and analyzing with said analytical instrument at least some of the trace constituents in said flow of gas;

the improvement comprising of reducing the pressure at said distal end of the gas sampling probe means by using a venturi effect caused by a flow of a transport gas supplied to said distal end.

In preferred methods the analytical instrument comprises a mass spectrometer, most preferably an atmospheric pressure ionization mass spectrometer. Thus a preferred method further comprises the steps of ionising in said entrance port at least some of said trace constituents present in the gas received therein, allowing at least some of the ions so generated to pass through inlet aperture means into an evacuated chamber, and mass analyzing at least some of the ions which enter said evacuated chamber. Preferably the ionization is achieved by sustaining a corona discharge in said entrance port.

The invention further provides a method of analyzing trace constituents present in the breath of a subject wherein the subject breathes through breathing tube means and at least some of the exhaled breath of the subject is sampled through the proximal end of said sampling probe means which is disposed in said breathing tube means.

It will be appreciated that the trace constituents present in the breath of a subject may be associated with the aroma and taste of a foodstuff or a drink being consumed by the subject at the time of sampling, or may be associated with the environment to which the subject is presently, or has previously been, exposed to. They may also be associated with a medical condition. The invention therefore further provides methods of analysis for these particular trace constituents.

The invention further provides a method of simultaneously determining a plurality of trace components present in a sample of gas or breath substantially as described wherein the mass spectrometer is operated in a multiple-ion monitoring mode so that selected mass-to-charge ratios characteristic of each of the trace constituents can be monitored substantially simultaneously. This method is particularly useful for flavour analysis because it is often desirable to monitor the release of many different trace constituents simultaneously, as it is the combination of many constituents which result in a characteristic flavour or aroma. In API mass spectrometry it is known that ions generated in a corona discharge can be fragmented by collisions with neutral molecules in the region immediately downstream of the counter electrode where the pressure is typically between 1 and 10 torr, and that the extent of that fragmentation can be controlled by adjusting the potential between the counter electrode and the inlet aperture of the mass analyzer. This potential determines the energy of the collisions between the ions and neutral molecules and therefore the extent of fragmentation. Preferred methods according to the invention therefore comprise the substantially simultaneous monitoring of a plurality of trace constituents present in a sample of gas using API mass spectrometry in a multiple-ion monitoring mode, wherein the difference in the potential at which the ions are generated and that at which they enter the ion mass analyzer is set automatically to a predetermined value according to the constituent species being monitored at any given instant, said predetermined values being selected to give a desired extent of fragmentation for the constituent species to which they apply, thereby enabling different degrees of fragmentation to be selected for different species during one the multiple-ion monitoring cycle of the mass spectrometer.

The invention further provides a method of analyzing the trace constituents comprised in a sample of gas in enclosed volume, such as the headspace in a vessel partially filled with a liquid or a solid. In such a method the proximal end of the sampling probe means is inserted into the enclosed volume or headspace so that some of the gas present in it is transferred to the entrance port of the analytical instrument and the trace constituents analyzed by means of the analytical instrument.

BRIEF DESCRIPTION OF THE DRAWINGS

Various embodiments of the invention will now be described in greater detail, by way of example only, and with reference to the figures, wherein.

DETAILED DESCRIPTION OF THE PREFERRED EMBODIMENT

Figure 1:
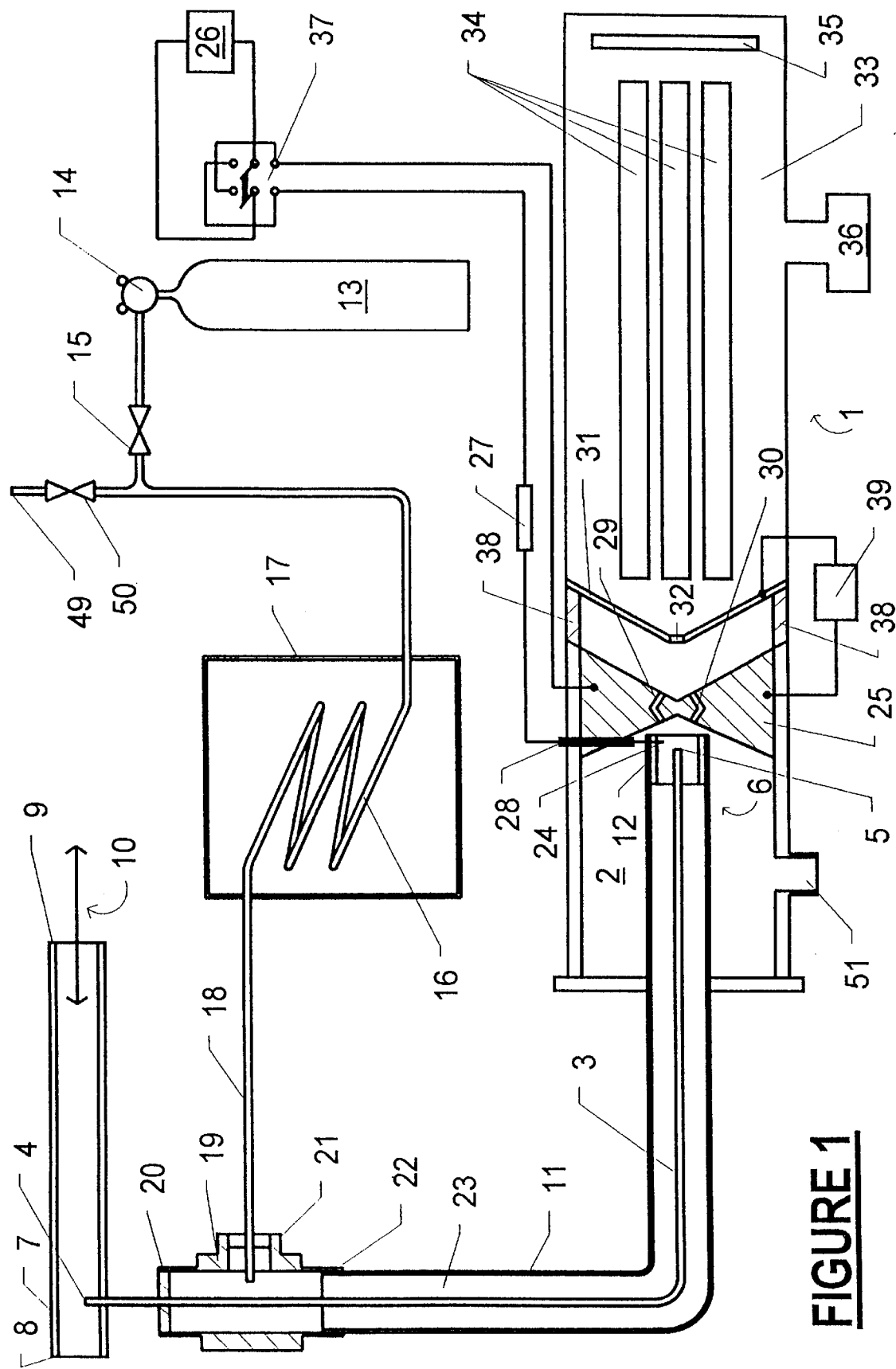
FIG. 1 is a schematic drawing of an API mass spectrometer according to the invention and suitable for the analysis of breath.

Referring to FIG. 1, an analytical instrument for analyzing trace constituents comprises an API mass spectrometer generally indicated by the numeral 1 which has an entrance port 2 and gas sampling probe means comprising a 0.53 mm inside diameter, 0.68 mm outside diameter capillary tube 3 made of deactivated fused silica. The capillary tube 3 has a proximal end 4 and a distal end 5. Means for reducing the pressure in the vicinity of the distal end 5 comprises a venturi means generally indicated by the numeral 6. The apparatus illustrated in FIG. 1 is intended for the analysis of exhaled human breath and to facilitate this a breathing tube 7 is in communication at its end 8 with the nostril (or mouth) of a subject. The other end 9 of the breathing tube 7 is open to the atmosphere so that alternate inhalations and exhalations by the subject pass through the tube 7, as indicated by the arrow 10. During exhalations the breathing tube 7 is therefore filled with the breath of the subject which contains the trace constituents to be analyzed.

The proximal end 4 of the capillary tube 3 is sealably inserted through the wall of the breathing tube 7 as shown in the figure. The venturi means 6 comprises an outer tubular member 11 disposed coaxially about the capillary tube 3 and extending about 6 mm beyond the distal end 5 of the capillary tube 3. The inside diameter of the outer tubular member 11 is 3.2 mm, reduced to 1.6 mm for a distance of 15 mm by a reducer 12, as shown in the figure. Transport gas (nitrogen) is introduced from a cylinder 13 through a regulator 14 and an isolating valve 15 through a coil 16 disposed in an oven 17, so that the transport gas flowing through the pipe 18, connected to the outlet of the coil 16, is at a temperature of at least 100° C. An additional inlet port 49 and an isolating valve 50 allow the introduction of additional or alternative chemical ionization reagents or other chemical species for chemical or physical modification of the sample gas, for example, removal of an unwanted interfering species by a specific reaction. Samples for calibrating the mass spectrometer may also be introduced into port 49. A 'T' connector 19 is fitted over the capillary tube 3 as shown, sealing the outside of that tube in its connection 20, the outside of the pipe 18 in connection 21, and the outside of the outer tubular member 11 in connection 22. Hot transport gas from pipe 18 is thereby directed to the annular space 23 between the outside of the capillary tube 3 and the inside of the outer tubular member 11 and heats the capillary tube to the desired temperature. The transport gas then flows coaxially over the distal end 5 of the capillary tube 3 into the entrance port 2, reducing as it does so the pressure in the vicinity of the distal end 5 by the venturi effect and thereby causes a flow of gas from the breathing tube 7 into the entrance port 2. With a nitrogen flow of approximately 10 l/min, a flow of sampled breath of about 50 ml/min can be created in this way in the capillary tube 3. A vent 51 discharges the majority of the gas entering the entrance port 2 to the atmosphere, maintaining the pressure in it at about that of the atmosphere. In order to minimise the response time of the apparatus, for example to facilitate its use for breath-by-breath analyses, the end of the outer tubular member 11 is disposed very close to the counter electrode 25 as shown in FIG. 1, minimising the volume of the ionization region.

In order to ionise the trace constituents in the breath entering the entrance port 2, ionising means are provided in the port 2 comprising a sharply pointed corona electrode 24 supported in an insulator 28, a counter electrode 25, and means for sustaining a corona discharge between them comprising a power supply 26, a 10 MΩ series resistor 27 and a polarity reversing switch 37. Power supply 26 is an adjustable supply having a range of 0–4 KV at a few milliamps. The voltage used is adjusted to give optimum ionization conditions. In order to permit the outer tubular member 11 to extend close to the counter electrode to define an ionization region of minimum dead volume, the corona electrode 24 is inserted through the wall of the tubular member 11, which is made of a PFA (perfluoroalkoxy) rubber to provide electrical insulation.

The counter electrode 25 comprises four passages, two of which are shown at 29 and 30, through which ions formed in the corona discharge are drifted towards the inlet aperture means by the flow of transport gas and sampled breath from the venturi means 6. The inlet aperture means comprises an electrically conductive diaphragm 31 in which a hole 32 (about 0.5 mm diameter) is formed. The counter electrode 25, insulated flange 38 (see below) and the inlet diaphragm 31 define a first pumping stage 52 in which the pressure is maintained between 1 and 10 torr by means of a vacuum pump (not shown). Ions pass through the hole 32 into an evacuated chamber 33 in which there is disposed ion mass analyzing means comprising a quadrupole mass filter 34 and an ion detector 35. It will be appreciated that the filter 34 and detector 35 are shown as representative major components of a conventional mass analyzer which also contains many minor components (not shown) such as ion lenses and, typically, further evacuated chambers. A high vacuum pump 36 is shown as representative of the pumping system of such a conventional analyzer, and maintains the pressure in the vicinity of the mass filter 34 at less than $10^{-4}$ torr.

As in all API corona discharge mass spectrometers, the discharge between the electrodes primarily generates positive ions when the corona electrode 24 is positive with respect to the counter electrode 25 and negative ions when the polarity is reversed. As both types of ions are of interest in the preferred applications of the apparatus, a polarity reversing switch 37, operable in conjunction with the control system of the mass analyzer, is provided to allow ions of either polarity to be generated and mass analyzed.

The counter electrode 25 and the housing of the entrance port 2 are mounted from the inlet aperture diaphragm 31 by an insulated flange 38 so that a potential difference (adjustable, up to about 50 volts, positive to the inlet aperture diaphragm 31 for positive ions) can be maintained between them by the power supply 39. The potential difference used controls the extent of fragmentation of the ions formed in the corona discharge because it determines the energy of the collisions between the ions and neutral gas molecules present in the region between the counter-electrode 25 and the electrically conductive diaphragm 31. The power supply 39 is a programmable supply, controlled by the mass spectrometer control system in such a way that its output potential may be set to any desired value at any given instant during a mass scan or during multiple-ion monitoring cycles of the spectrometer. This allows different predetermined potentials to be set for each ion species monitored, and provides the option of causing different extents of fragmentation for each ion species monitored during a single multiple-ion-monitoring cycle. This is especially useful, for example, if it is desired to simultaneously monitor constituents which produce pseudo-molecular ions of the same mass-to-charge ratio. By setting different extents of fragmentation for the two ion species it may be possible, for example, to monitor one ion species at its pseudo-molecular ion while the other species is caused to fragment and can be monitored at the mass of a characteristic fragment without interfering with the first species.

Figure 2:
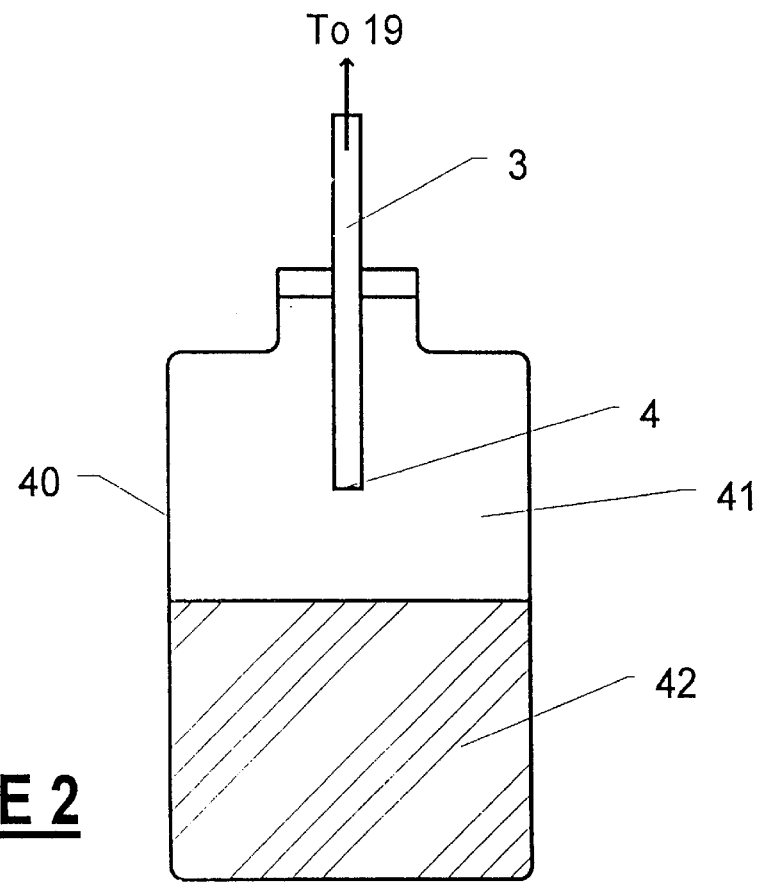
FIG. 2 is a drawing of part of apparatus according to the invention suitable for the analysis of gas contained in an enclosed volume.

FIG. 2 shows an alternative embodiment of the invention for sampling gases containing trace constituents from an enclosed volume. In this example, the proximal end 4 of the capillary tube 3 is sealably inserted into the headspace 41 of a vessel 40 which also contains a liquid 42. The venturi pumping effect described previously is used to extract a sample of gas from the headspace and transfer it to the entrance port 2 of the mass analyzer. It will be appreciated that by connecting the proximal end 4 of the capillary tube 3 with a syringe needle and using sample vessels with closures comprising a septum, a conventional autosampler can be used to provide automatic analysis of many samples.

Figure 3:
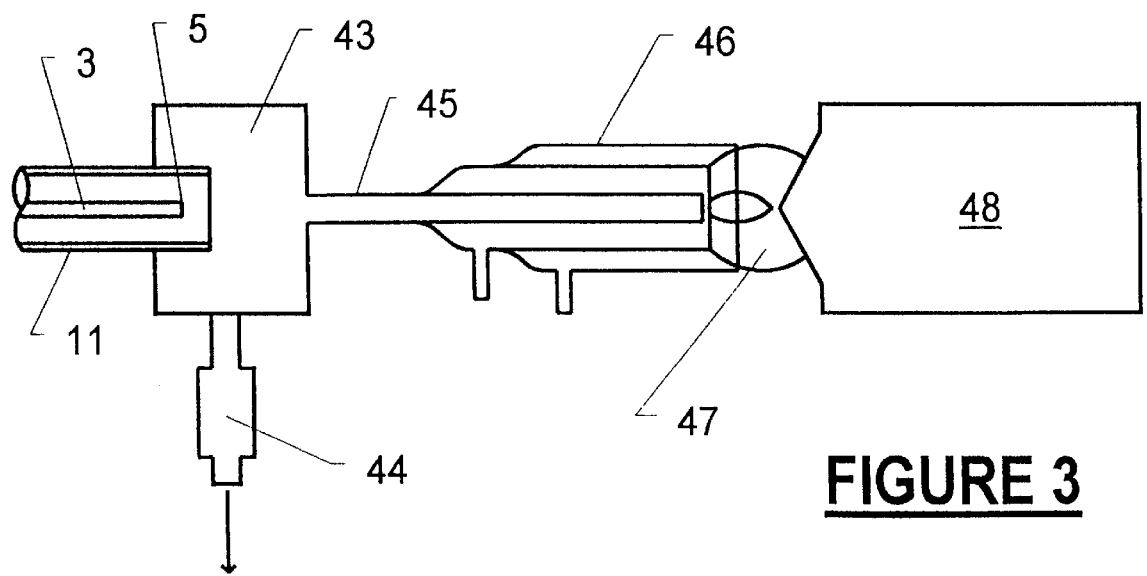
FIG. 3 is a schematic drawing of part of an ICP mass spectrometer according to the invention.

FIG. 3 shows an embodiment of the invention using an ICP or MIP mass analyser. In this case, the distal end 5 of the capillary tube 3 and the outer tubular member 6 are disposed in a buffer chamber 43 having a restrictor 44 leading to the atmosphere to generate a pressure inside the chamber 43 slightly greater than atmospheric. An outlet 45 from the chamber 44 is connected to the inlet of a conventional ICP torch 46 which generates a plasma 47. Ions generated in the plasma 47 may then be analyzed in a conventional ICP mass spectrometer 48. Power for generating the plasma 47 may be obtained as in conventional ICP or MIP spectrometers from a coil surrounding the torch 46 or by disposing the torch in a microwave cavity. Use of ICP or MIP mass spectroscopy is appropriate when elemental or isotopic analyses of the sample gas are required.

What is claimed is:

1. In apparatus for analyzing trace constituents in a sample of gas, said apparatus comprising:

an analytical instrument for analyzing at least some of said trace constituents and having an entrance port;

gas sampling probe means through which at least some of said gas may flow and having a proximal end disposed for communication with a gas to be analyzed and a distal end disposed in communication with said entrance port; and means for reducing the pressure in the vicinity of said distal end relative to that at said proximal end so that at least some of the gas to be analyzed flows to said entrance port;

the improvement comprising said means for reducing the pressure comprising venturi means disposed adjacent to said distal end, and means for causing a flow of a transport gas to said venturi means.

2. Apparatus as claimed in claim 1, wherein said analytical instrument comprises a mass spectrometer, said mass spectrometer further comprising:

ionisation means, operable at atmospheric pressure, for ionising at least some of said trace constituents and disposed in said entrance port;

inlet aperture means through which ions generated by said ionization means may pass, said inlet aperture means connecting said entrance port with an evacuated chamber; and ion mass analyzing means disposed in said evacuated chamber for receiving ions passing through said inlet aperture means and for producing signals indicative of their mass-to-charge ratio and their quantity.

3. Apparatus as claimed in claim 2, wherein said ionization means comprise a corona electrode and a counter electrode both disposed in said entrance port, said counter electrode being further disposed between the distal end of the gas sampling probe means and the inlet aperture means, and said corona electrode being further disposed between the distal end of the gas sampling probe means and the counter electrode, and means for sustaining a corona discharge between said corona electrode and said counter electrode.

4. Apparatus as claimed in claim 2, wherein said venturi means comprises an outer tubular member disposed coaxially about said gas sampling probe means, said outer tubular member extending a short distance beyond the end of the gas sampling probe means, and wherein said outer tubular member is arranged so that said transport gas is caused to flow through said outer tubular member thereby causing a pressure reduction in the vicinity of the distal end of the gas sampling probe means.

5. Apparatus as claimed in claim 2, further comprising breathing tube means for receiving exhaled breath from the nose or mouth of a subject, said breathing tube means being open to the atmosphere at the end remote from the subject and being disposed so that at least some exhaled breath of the subject passes through said breathing tube means, and wherein the proximal end of said sampling probe means is disposed within said breathing tube means.

6. Apparatus as claimed in claim 1, wherein said transport gas comprises nitrogen.

7. Apparatus as claimed in claim 1, wherein means are also provided for introducing into said gas sampling probe means one or more additional chemical ionization reagents, or a calibration sample for said analytical instrument.

8. Apparatus as claimed in claim 1, wherein said analytical instrument comprises a mass spectrometer comprising a plasma ionization source having a sample inlet for receiving gas from the distal end of the gas sampling probe means, and wherein said transport gas is chosen from the group consisting of argon and helium.

9. Apparatus as claimed in claim 1, wherein said gas sampling probe means comprises a capillary tube made of deactivated fused silica.

10. Apparatus as claimed in claim 1, wherein said venturi means comprises an outer tubular member disposed coaxially about said gas sampling probe means, said outer tubular member extending a short distance beyond the end of the gas sampling probe means, and wherein said outer tubular member is arranged so that said transport gas is caused to flow through said outer tubular member thereby causing a pressure reduction in the vicinity of the distal end of the gas sampling probe means.

11. Apparatus as claimed in claim 10, wherein said outer tubular member extends beyond the end of said gas sampling probe means by a distance of between 0.2 and 2 cm.

12. Apparatus as claimed claim 10, wherein the flow rate of said transport gas is between 5–10 l/minute.

13. Apparatus as claimed in claim 1, further comprising breathing tube means for receiving exhaled breath from the nose or mouth of a subject, said breathing tube means being open to the atmosphere at the end remote from the subject and being disposed so that at least some exhaled breath of the subject passes through said breathing tube means, and wherein the proximal end of said gas sampling probe means is disposed within said breathing tube means.

14. Apparatus as claimed in claim 1, further comprising means for heating said gas sampling probe means to at least 100° C.

15. A method of analyzing trace constituents comprised in a sample of gas, said method comprising the steps of:

providing an analytical instrument for analyzing at least some of said trace constituents, said analytical instrument having an entrance port;

providing a gas sampling probe means through which at least some of said gas may flow and having a proximal end and a distal end;

disposing said proximal end of said gas sampling probe means in communication with the gas to be analyzed;

disposing said distal end of said gas sampling probe means in communication with said entrance port;

reducing the pressure in the vicinity of said distal end relative to that at said proximal end so that at least some of the gas to be analyzed flows to said entrance port; and analyzing with said analytical instrument at least some of the trace constituents in said flow of gas;

the improvement comprising of reducing the pressure at said distal end of the gas sampling probe means by using a venturi effect caused by a flow of a transport gas supplied to said distal end.

16. A method as claimed in claim 15, wherein said transport gas is caused to flow substantially coaxially over the distal end of said gas sampling probe means.

17. A method as claimed in claim 15, wherein said analytical instrument comprises an atmospheric pressure ionization mass spectrometer.

18. A method as claimed in claim 17, further comprising the steps of ionising in said entrance port at least some of said trace constituents present in the gas received therein by means of a corona discharge established between a corona electrode and a counter electrode, and, allowing at least some of the ions so generated to pass through inlet aperture means into an evacuated chamber, and mass analyzing at least some of the ions which enter said evacuated chamber.

19. A method as claimed in claim 18, wherein the potential between said counter electrode and said inlet aperture means is adjusted to an optimum value previously determined according to the ionic species transmitted at any instant by said mass spectrometer.

20. A method as claimed in claim 18, wherein the pressure in the region immediately downstream of the counter electrode is maintained between 1 and 10 torr so that said ions undergo collisions with neutral molecules and at least some of them undergo fragmentation, and wherein the extent of said fragmentation is controlled by adjusting the potential difference between the counter electrode and the inlet aperture means of the mass analyzer.

21. A method as claimed in claim 20, wherein said mass spectrometer is operated in a multiple-ion monitoring mode, thereby allowing the substantially simultaneous monitoring of a plurality of trace constituents present in said sample of gas, and wherein said potential difference is set automatically to an optimal predetermined value according to the mass-to-charge ratio which said mass spectrometer is set to monitor at any given instant, said optimal predetermined values being selected to give a desired extent of fragmentation for the constituent species to which they apply, thereby enabling different degrees of fragmentation to be selected for different ions during one the multiple-ion monitoring cycle of the mass spectrometer.

22. A method as claimed in claim 17, wherein said sample gas comprises the breath of a subject, said method further comprising the steps of:

disposing the proximal end of said gas sampling probe means in a breathing tube means;

passing at least some of the exhaled breath of a said subject through said breathing tube means; and sampling through the proximal end of said gas sampling probe means at least some of said exhaled breath.

23. A method as claimed in claim 17, wherein said mass spectrometer is operated in a multiple-ion monitoring mode so that selected mass-to-charge ratios characteristic of each of the trace constituents can be monitored substantially simultaneously.

24. A method as claimed in claim 15, wherein said analytical instrument comprises a plasma ionisation mass spectrometer.

25. A method as claimed in claim 15, wherein said sample gas comprises the breath of a subject, said method further comprising the steps of:

disposing the proximal end of said gas sampling probe means in a breathing tube means;

passing at least some of the exhaled breath of a said subject through said breathing tube means; and sampling through the proximal end of said gas sampling probe means at least some of said exhaled breath.

26. A method as claimed in claim 25, wherein said sample of exhaled breath is analyzed while the subject is eating or drinking.

27. A method as claimed in claim 15, wherein said sample of gas is contained in an enclosed volume and wherein the proximal end of the gas sampling probe means is inserted into said enclosed volume so that at least some of the gas present in said enclosed volume is transferred to said entrance port.

28. A method as claimed in claim 27, wherein said enclosed volume is the headspace in a vessel partially filled with a liquid or a solid.

29. A method as claimed in claim 15, wherein a said sample of gas is taken adjacent to a surface which is either emitting a fragrance or to which a fragrance has been applied, said method further comprising the step of disposing the proximal end of said gas sampling probe means close to a said surface whereby molecules characteristic of said fragrance are drawn into said gas sampling probe means and are analyzed substantially in real-time.

* * * * *